United States Patent [19]
Wu et al.

[11] Patent Number: 5,833,615
[45] Date of Patent: Nov. 10, 1998

[54] EXCITATION ENHANCED ULTRASOUND SYSTEM

[75] Inventors: Yunqiu Wu, Cherry Hill, N.J.; Flemming Forsberg, Philadelphia; Barry Goldberg, Conshohocken, both of Pa.

[73] Assignee: Thomas Jefferson University, Philadelphia, Pa.

[21] Appl. No.: 853,967

[22] Filed: May 9, 1997

[51] Int. Cl.$^6$ ........................................ A61B 8/00
[52] U.S. Cl. ................................................. 600/458
[58] Field of Search ................................ 600/439, 458

[56] References Cited

U.S. PATENT DOCUMENTS

| | | | |
|---|---|---|---|
| 3,968,680 | 7/1976 | Vopilkin et al. | 73/67.8 R |
| 4,276,885 | 7/1981 | Tickner et al. | 600/458 |
| 4,519,260 | 5/1985 | Fu et al. | 73/861.25 |
| 4,718,433 | 1/1988 | Feinstein | 600/458 |
| 4,815,043 | 3/1989 | Shirasaka | 367/7 |
| 5,255,683 | 10/1993 | Monaghan | 600/458 |
| 5,425,366 | 6/1995 | Reinhart et al. | 600/458 |
| 5,433,207 | 7/1995 | Pretlow, III | 128/662.02 |
| 5,456,257 | 10/1995 | Johnson et al. | 600/458 |
| 5,526,816 | 6/1996 | Arditi | 128/662.02 |
| 5,540,909 | 7/1996 | Schutt | 424/9.52 |
| 5,560,364 | 10/1996 | Porter | 128/662.02 |

OTHER PUBLICATIONS

Barry B. Goldberg et al., Rev. "*Ultrasound Contrast Agents: A Review*", vol. 20, No. 4., pp. 319–333, (1994).

Laurence Needleman et al., Ultrasound Quarterly, "*Contrast Agents in Ultrasound*", vol. 13, No. 3. pp. 121–138, (1996).

Church, J. Acoust. Soc. Am. 97 (3), pp. 1510–1521 (Mar. 1995).

Flynn, J. Acoust. Soc. Am. 84 (3), pp. 985–998 (Sep. 1988).

Thomas R. Porter and Feng Xie, Cir., vol. 92, No. 9, pp. 2391–2395 (1995).

Hogg, Physiological Rev., 67, pp. 1249–1295, (1987).

de Jong et al., Ultrasonics, 32(6), pp. 447–453, (1994).

Mor–Avi et al., J.Am.Coll. Cardiol., 24(7), pp. 1779–1785, (1994).

*Primary Examiner*—Marvin M. Lateef
*Assistant Examiner*—Maulin Patel
*Attorney, Agent, or Firm*—Seidel, Gonda Lavorgna & Monaco, PC

[57] ABSTRACT

The present invention relates generally to an ultrasound system and method, and more particularly to an excitation enhanced ultrasound system and method. The system employs at least one excitation signal as a "flashlight" for exciting ultrasonic microbubbles contained in an ultrasound contrast agent. The system further employs at least one ultrasound imaging signal for imaging structures and blood flow within an object. The excitation signal excites and expands the microbubbles which increase the amount of returned ultrasound imaging signals scattered and returned by an object. This process increases the signal to noise ratio of the returning imaging signal sufficiently to provide exciter weighted imaging, blood pool imaging, and harmonic imaging, facilitating improved diagnostic ultrasound and therapeutic ultrasound.

12 Claims, 9 Drawing Sheets

EXCITATION ENHANCED ULTRASOUND SYSTEM

FIELD OF THE INVENTION

The present invention relates generally to an ultrasound system and method, and more particularly to an excitation enhanced ultrasound system and method employing at least one ultrasound excitation signal for exciting microbubbles contained in an ultrasound contrast agent. The microbubbles, when excited, increase the amount of image producing ultrasound energy scattered and returned (echoed) by the contrast agent. This phenomenon substantially increases the signal to noise ratio (SNR) and consequently the detection and imaging of the returned ultrasound energy. By increasing the amount of returned ultrasound energy from the contrast agent, the invention can provide exciter weighted imaging, blood pool imaging, and harmonic imaging to facilitate more accurate diagnoses and improved ultrasound therapy.

BACKGROUND OF THE INVENTION

Medical ultrasound technology is known and commonly used to study anatomical structures, characterize tissue, measure blood flow, and provide ultrasound therapy within the body. Ultrasound systems typically energize a transducer which transmits short pulses of image producing ultrasound energy into the body. The ultrasound energy is returned by acoustic interfaces with the body. The returned ultrasound energy is received by the transducer and converted into an electrical signal which is used to produce an ultrasound image.

Conventional ultrasound equipment employ a type of imaging known as B-mode. In B-mode, an ultrasound system will exploit the amplitude of returned ultrasound energy that is detected and measured as a function of time to construct dynamic or static images of structures within a body. These images represent a tomographic view through the body.

In addition to imaging anatomical structures, ultrasound systems can acquire and image the velocity of blood flow by using pulsed Doppler signal processing. A Doppler shift, characterized by a shift in frequency of returned ultrasound energy, occurs when ultrasound strikes moving blood cells. From the Doppler shift, the direction and velocity of blood flow can be detected and imaged. In addition, a spectral Doppler system can be used to display the direction, in addition to the magnitude, of blood flow as a function of time. Other improvements in conventional ultrasound include color flow mapping, where color is superimposed on the B-mode images to highlight blood flow imaging when displayed in color.

Ultrasound also has a therapeutic use. In therapeutic applications, it is often necessary to have specific agents delivered to targeted regions in the body by ultrasound. When delivered, the agents are activated by therapeutic ultrasound which may comprises higher levels of ultrasound energy. After applying therapeutic ultrasound, the agent's therapeutic progress often needs to be continuously monitored by diagnostic ultrasound.

Although ultrasound has been available for some time, significant disadvantages and deficiencies in conventional ultrasound systems are known. The use of the term "conventional" refers to ultrasound systems that do not employ the teaching of the present invention. One significant deficiency in conventional ultrasound systems is the limited ability to image blood flow within deep lying and small blood vessels in the body. Another significant deficiency in conventional ultrasound systems is the use of wall filters for Doppler imaging. Wall filters are known to limit the ability of ultrasound systems to detect blood flow in small blood vessels.

Many past attempts to solve this very important problem have failed or have produced only modest improvements. One such attempt to improve blood flow imaging is the addition of ultrasonic contrast agents into the structures and blood flow within the body. Microparticles act as effective acoustic scathers and thus increase the strength of signals scattered from blood flow. Contrast agents are continuously being developed and refined to improve the imaging of blood flow.

Contrast agents, such as Albunex®, contain encapsulated microbubbles having a size measured by their radius which is generally between 0.5 and 10.0 um. Microbubbles will interact with ultrasound energy causing it to scatter. When the microbubbles are introduced into the body and exposed to ultrasound, they typically increase the amount of ultrasound energy scattered by tissue or blood flow.

It is therefore known that the administration of a contrast agent having microbubbles of the appropriate size can facilitate the differentiation and imaging between normal and pathological areas in the body.

The amount of ultrasound energy that is scattered and returned by contrast agents is mainly a function of microbubble size and the frequency and pressure of the ultrasound energy. For a given ultrasound frequency, there corresponds a microbubble resonance size. The effective scattering strength of microbubbles increases with microbubble size, and reaches a peak at microbubble resonance size. The fundamental components increase with microbubble size, while the harmonic components decrease with microbubble size. (C. C. Church, "The effects of an elastic solid surface layer on the radial pulsations of gas microbubbles," J. Acoust. Soc. Am. Vol. 97, No. 3, pp. 1510–1521, 1995). When f=2.5 $MH_z$, the microbubble resonance size=4.2 $\mu$m for albunex microbubbles. Microbubbles equal to and larger than 4 $\mu$m comprise only 10 percent of all available microbubbles.

Administration of contrast agents often reduce contrast between the region of interest and its surrounding anatomical structures. Microbubbles that are too small to scatter ultrasound can dampen the ultrasound energy that is scattered negatively affecting echo intensity and the image produced by targeted anatomical structures. Several unsuccessful attempts have been made to correct the problem of dampened echo intensity. For example, practitioners have been known to increase the level of ultrasound energy emitted in order to effect a like increase in echo intensity.

By increasing the ultrasound power, the longevity of the microbubbles is known to be severely shortened.) Intermittent or transient response imaging has been used to alleviate the problem of microbubble destruction (Thomas R. Porter and Feng Xie, Circulation, Vol. 92, No. 9, pp. 2391–2395, 1995). In Porter, pulsed ultrasound is triggered and received to determine the cardiac cycle using commercially available scanner. This technique limits the frame rate available for diagnosis. Others have attempted to increase the amount of contrast agent present in the structure. However, the effectiveness of this practice is variable and generally unsuccessful due to a subsequent increase in attenuation known as a "shadowing" artifact.

The present invention solves the above-described problems encountered with conventional ultrasound equipment and contrast agents. In addition to solving these problems, the present invention provides conventional ultrasound equipment with new and important features such as exciter weighted imaging, blood pool imaging, and harmonic imaging using wide band echo signal detection. The significant feature of present invention is that it enables conventional ultrasound equipment to properly exploit its own capabilities as well as those of ultrasound contrast agents.

SUMMARY OF THE INVENTION

The present invention is an excitation enhanced ultrasound imaging system and method employing at least one ultrasound excitation signal serving as a "flashlight" for exciting microbubbles contained in an ultrasound contrast agent. In the present invention, conventional ultrasound equipment can be made to image structures and blood flow, including deep lying and small blood vessels, by exploiting the scattering and harmonic generative behavior of ultrasound contrast agents when exposed to ultrasound excitation and imaging signals.

The excitation enhanced ultrasound system includes at least one exciter for transmitting an excitation signal capable of exciting microbubbles contained in an object. The system further includes a conventional ultrasound system in operative communication with the exciter. The conventional ultrasound system is capable of transmitting at least one imaging signal, as well as receiving the imaging signals that are scattered and returned by both the microbubbles and the object.

The system further includes a pulse controller operatively coupled to the exciter and the conventional ultrasound system. The pulse controller controls the transmitting of the excitation signals and the receiving of the imaging signals according to a sequence. The conventional ultrasound system produces an image from the received imaging signals using conventional pulse-echo techniques.

The present invention also provides a method for an excitation enhanced ultrasound system including steps of exciting microbubbles in an object, imaging ultrasound signals scattered and returned by the object, and sequencing the exciting and received imaging signals to produce an exciter weighted image, blood flow image, or harmonic image.

In the method, exciting the microbubbles is accomplished by at least one exciter transmitting an excitation signal capable of exciting the microbubbles contained in an object. Imaging is accomplished by a conventional ultrasound system in operative communication with the exciter. The conventional ultrasound system is capable of transmitting at least one imaging signal and capable of receiving the imaging signals that are scattered and returned by the microbubbles and the object. Sequencing is accomplished by a pulse controller operatively coupled to the exciter and the conventional ultrasound system. The pulse controller controls the transmitting of the excitation signals and the receiving of the imaging signals according to a sequence. The conventional ultrasound system produces an image from the received imaging signals using conventional pulse-echo techniques.

It is known that a contrast agent containing microbubbles will scatter and return ultrasound energy with fundamental as well as harmonic components. The excitation signal will momentarily expand microbubbles and enhance their ability as harmonic scatters. These enhanced harmonic products are used by the present invention to produce an enhanced harmonic image of blood flow in deeper lying and small blood vessels. The invention can also more readily distinguish ultrasound energy scattered and returned from tissue having a contrast agent from tissue without a contrast agent.

For example, by transmitting ultrasound energy at a fundamental imaging transducer frequency (f) and receiving returned ultrasound energy from the contrast agent at a second harmonic (2f), a preferred image of the anatomical structures containing the contrast agent can be produced. By using an additional excitation field, the present invention therefore produces stronger harmonic components and thus, a superior result over conventional ultrasound equipment because it can distinguish and reduce undesirable returned ultrasound energy. The present invention therefore provides ultrasound images of the most preferred anatomical structures having a contrast agent and reduces the images of the least preferred surrounding tissue without the contrast agent.

The invention includes a pulse sequencing technique for simultaneously forming an exciter weighted image and a conventional ultrasound image in order to facilitate diagnosis. Additionally, the excitation enhancing technique and a wideband signal detection feature increase the signal to noise ratio and facilitate harmonic imaging. The latter feature provides improved detection of low or weak blood flow in the body.

In particular, the excitation technique covered in the present invention uses an additional ultrasound or acoustic field generated by an acoustic element as a "flashlight". The excitation field excites the microbubbles and thus increase momentarily their effective scattering capability. The word flashlight as used here means that the microbubbles are made more perceptible to the imaging pulse, just as a flashlight allows an image to be seen in darkness. This is accomplished through the increase of overall size of the microbubbles and the number of microbubbles close to and above a resonance size.

The present invention also includes a pulse sequencing technique to control the excitation of the exciter and the transmitter as well as a gated echo receiving process. With the proper pulse sequences, an exciter weighted image and a non-weighted (conventional) ultrasound image can be formed and displayed simultaneously to facilitate diagnosis.

In one aspect of the invention, an exciter and a conventional ultrasound system utilize a single combined transmitting and receiving transducer. The transducer comprises a component capable of emitting an excitation signal, and a component capable of emitting and receiving the scattered and returned imaging signal. In another aspect of the invention, the transducer comprises a separate element for transmitting the image signal and a separate element for receiving the imaging signal.

In another aspect of the invention, cyclic variations of echogenecity due to heart motion or breathing activity are considered. In the invention it is advantageous, but not necessary, to couple pulse sequencing and the heart's activities via an electrocardiograph (EKG) device.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

The present invention is an excitation enhanced ultrasound system and method for producing enhanced imaging of anatomical structures and blood flow in a body when using ultrasound contrast agents. Enhanced imaging is produced by an excitation feature, described in detail below, which allows the present invention to enhance the pulse-echo ultrasound energy returned by targeted tissue or blood flow containing ultrasound contrast agents. An important aspect of the present invention is that it is adaptable to conventional ultrasound equipment.

The excitation feature of the present invention provides otherwise conventional ultrasound equipment with the additional capabilities of exciter weighted imaging, harmonic imaging with wideband echo signal detection, and enhanced blood pool imaging. These imaging capabilities are made possible by a dramatically increased signal to noise ratio produced by the excitation feature.

Another important aspect of the invention is a pulse sequencing process, described in detail below, for controlling the excitation of the invention's exciter, transmitter, and receiver components. The pulse sequencing process controls the gated echo receiving process, also described in detail below. With the proper pulse sequencing, an exciter weighted image and a non-weighted (conventional) ultrasound image can be acquired and displayed simultaneously. This feature provides image discrimination that would not be possible in conventional equipment. In addition, with enhanced blood pool imaging, blood flow can be imaged even in areas where a pool may be present, which is not possible by means of conventional ultrasound.

The invention further includes a transducer arrangement capable of producing an excitation signal and an imaging signal, and receiving returned ultrasound energy.

Figure 1:
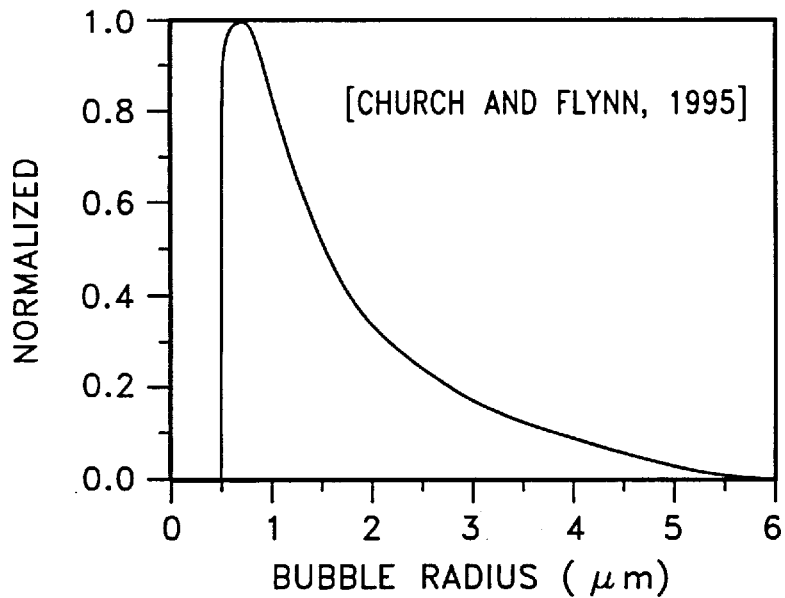
FIG. 1 is a graphical representation of normalized size and radius of microbubbles of a contrast agent, specifically Albunex®.

Referring to FIG. 1, contrast agents such as Albunex® have a typical, but not exclusive, microbubble size (radius) distribution from 0.5 to 10 um, and a mean size distribution around 2 to 4 um. However, for albunex nearly 80 percent of all microbubbles have a size below 2 $\mu$m (Hogg, Physiological Rev., 67, pp. 1249–1295, 1987). Although there are microbubbles larger than 10 um, they are filtered out of the blood through pulmonary circulation.

All microbubbles will scatter ultrasound (acoustic) energy at a particular frequency. However, conventional ultrasound equipment typically operates between 2 and 10 MHz and therefore can only excite microbubbles having a size around 2 to 5 um. As a consequence of this limitation, only about 20 percent of all microbubbles are available to scatter ultrasound energy efficiently by conventional ultrasound equipment.

FIGS. 2 through 5 show the relationship between frequency and microbubbles size (radius) as determined by Church (Church, *J. Acoust. Soc. Am.*, 97(3), pp. 1510–1521, 1995).

Figure 2:
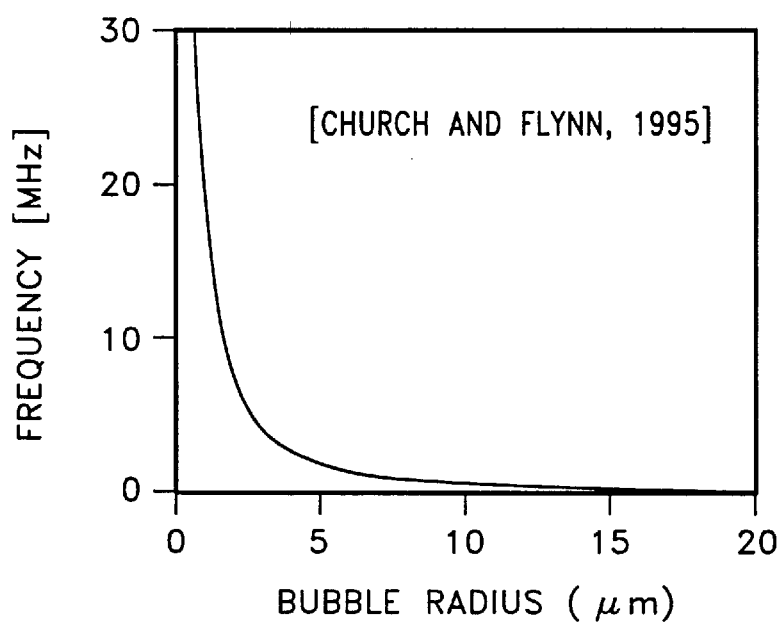
FIG. 2 is a graphical representation of resonant frequency response and radius of microbubbles of Albunex®.
Figure 3:
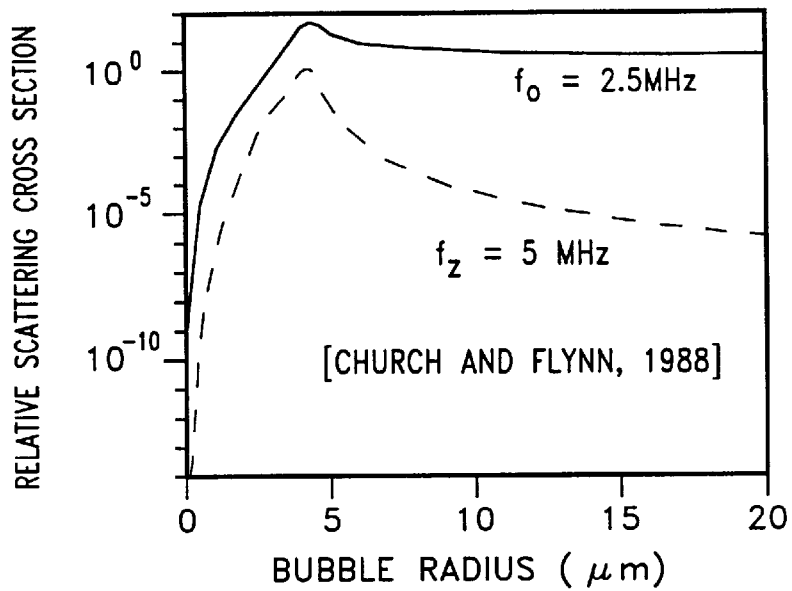
FIG. 3 is a graphical representation of relative cross section and radius of Albunex® microbubbles showing scattered acoustic energy at a fundamental and second harmonic resonant frequency.

FIG. 2 shows that the resonant frequency of microbubbles having a radius between 2.5 and 4.2 um decreases from 7.3 to 2.5 MHz respective. FIG. 3 shows that the maximum relative cross section of Albunex® microbubbles is achieved at a radius of 4.2 um when excited with ultrasound energy at a frequency of 2.5 MHz. Microbubbles above 4.2 um have a relative cross section slightly below the peak, producing a substantial amount of scattered ultrasound energy. However, microbubbles below 4.2 um have an exponentially decreasing cross section and produce significantly less scattered ultrasound energy. Therefore, increasing the size of the microbubbles that are below 4.2 um to a size that is at least 4.2 um or greater will result in a significant increase in the microbubble's relative cross section and the amount of scattered ultrasound energy.

The present invention recognizes the problem described above and solves it by increasing the size of the microbubbles that are below 4.2 um by exciting them with an ultrasound excitation signal. In a preferred mode of operation, the excitation signal is applied at a frequency in a range of 50 KHz to 10 MHz with a pulse repetition frequency between 0.5 Hz and 20 KHz, and a peak pressure of at least 100 kPa. It is recognized that other frequencies, repetition frequencies, and pressures can also be applied depending upon the contrast agents used.

The effect of resonance response and microbubble size as a function of frequency for gas microbubbles is described in detail by Church (*J. Acoust. Soc. Am.*, 97(3), pp. 1510–1521, 1995) and Flynn and Church (*J. Acoust. Soc. Am.*, 84(3), pp. 985–998, 1988), which are incorporated herein by reference.

It is known that ultrasound energy scattered by microbubbles has a total frequency response comprising the fundamental frequency of the source ultrasound energy and harmonic components of the source ultrasound energy above and below its fundamental frequency.

The present invention includes a wideband receiving means to detect over a wide frequency range the enhanced ultrasound components scattered by the contrast agent so that harmonic imaging of the anatomical structures can be formed.

Figure 4:
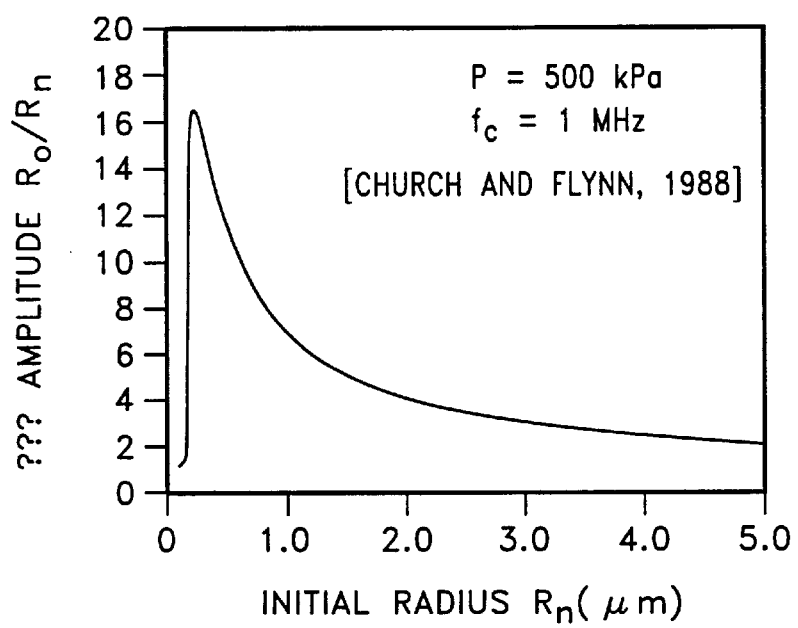
FIG. 4 is a graphical representation of relative radius expansions of ideal gas microbubbles excited by an acoustic field at a pressure amplitude of 500 kPa and a center frequency of 1 MHz.

FIG. 4 shows the relative radius expansion of ideal gas microbubbles when they are excited by an acoustic field at a pressure amplitude of 500 kPa and a center frequency of 1 MHz. It can be seen that under excitation, microbubbles will experience oscillation, expansion, collapse, and rebound. Both theoretical simulation and experimental investigation have indicated that it is possible to momentarily increase microbubble size. Flynn and Church (referenced above) found by numerical calculation that sub-micron and micron sized microbubbles experience "forced" oscillation and instantaneous microbubble growth during the first few cycles of continuous ultrasound.

The higher the excitation frequency, the smaller the relative microbubble expansion $R/R_0$ for a given acoustic pressure. The larger the applied pressure amplitude, the larger the $R/R_0$. Similarly, microbubbles in contrast agents will also undergo microbubble expansion under a suitable excitation field (de Jong et al., *Ultrasonics*, 32(6), pp. 447–453, 1994 which is incorporated herein by reference). As stated earlier, more than 80 percent of all microbubbles cannot scatter energy most efficiently at the frequencies produced by conventional equipment. Therefore, the phenomenon of instantaneous microbubble growth coupled with an excitation field increasing the size of the microbubbles to resonance by the ultrasound energy produced by conventional ultrasound equipment serves to substantially improve imaging performance.

Figure 5:
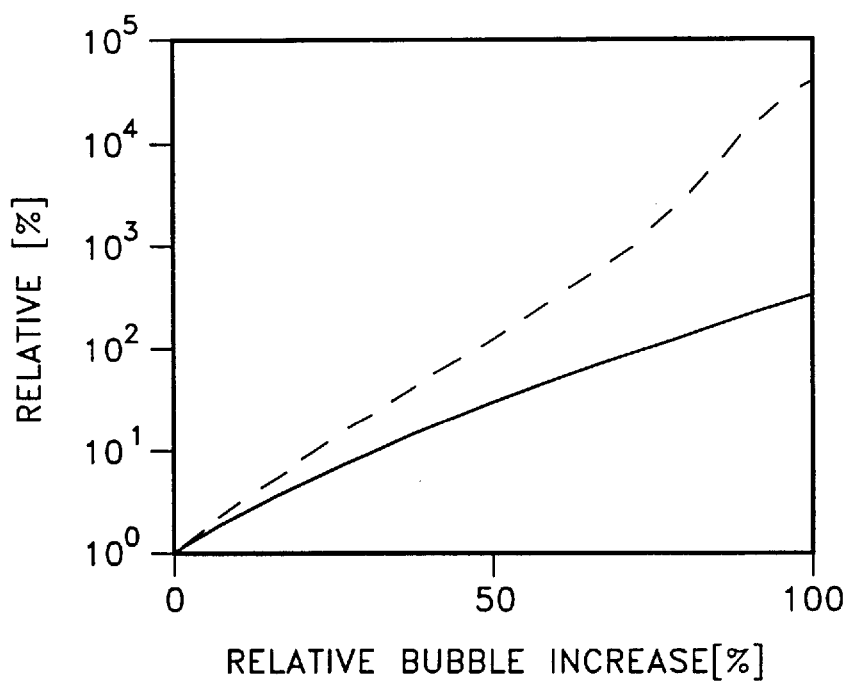
FIG. 5 is a graphical representation of relative change of total cross section and relative radius increase of Albunex® microbubbles under uniform expansion.

FIG. 5 shows the relative change of total cross section and relative radius increase of Albunex® microbubbles, assuming uniform microbubble expansion. As shown in FIG. 5, for a modest increase in size of just 30%, the microbubbles will experience a tenfold increase in total scattering cross section when excited at a frequency of 2.5 MHz and a pressure of 100 kPa. Although a uniform expansion is assumed, it is important to point out that the exact magnitude of microbubble expansion depends on the characteristics of the excitation signal and initial microbubble size.

As described above, the amount of scattered ultrasound energy from a contrast agent is determined by the size of the microbubbles and the frequency of the ultrasound signal. By using an additional excitation signal an exciter weighted image can be formed to selectively enhance the image produced from anatomical structures where contrast agents have been absorbed.

By adapting this technique to a conventional ultrasound system the non-weighted (conventional) image can be acquired and displayed with an exciter weighted image to facilitate diagnosis. The only differences between the two images exist in areas which contain contrast microbubbles. An excitation field will cause an instantaneous expansion of microbubbles and thus increase momentarily the effective scattering capability of microbubbles in two ways.

First, the effective scattering capability of these microbubbles increases significantly with their sizes. Because ultrasound (acoustic) scattering is a function of microbubble cross section, as the cross section increases more ultrasound energy is scattered and therefore returned for detection.

Second, scattering at the fundamental and the second harmonic of the fundamental will increase when more microbubbles are near and above the resonance size. Since a majority of microbubbles in an ultrasound contrast agent have a size well below the resonance size, an excitation field substantially increases the number of microbubbles close to resonance and thus the magnitude of the imaging signals (fundamental as well as harmonic) returned by the tissue or blood flow containing the microbubbles under excitation.

Figure 6:
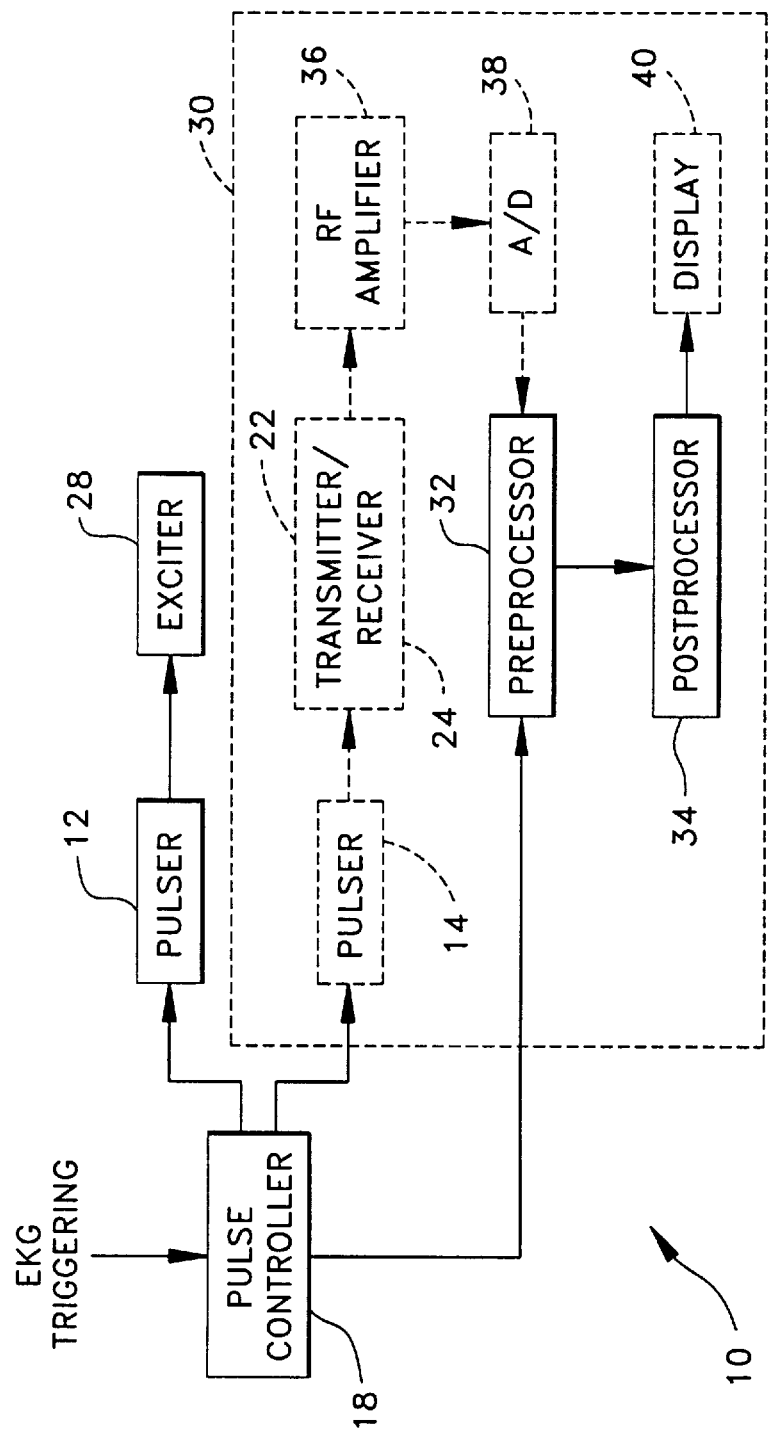
FIG. 6 is a block diagram of an excitation enhanced ultrasound system according to the present invention.

Referring to FIG. 6, there is illustrated an enhanced excitation ultrasound system 10 according to the present invention. The system has an exciter 28 driven by a pulser 12 for emitting at least one excitation signal. At least one excitation signal, preferably having a pulse waveform, is produced by an acoustic element (not shown) driven by the pulser 12. Parameters of the excitation signal, such as its center frequency, duration, repetition frequency, and amplitude, are chosen in order to cause the optimum excitation and expansion of the selected microbubbles contained in a specific area of interest.

The excitation signal should have a center frequency in a range of frequencies between 50 kHz to 10 MHz, and preferably between 0.5 and 3.0 MHz. However, it is understood that the excitation signal can be below 50 kHz and above 10 MHz. The frequency can be selected as required to excite and expand selected microbubbles of the particular contrast agent used during the ultrasound examination.

The duration of the excitation signal should have a range between 0.1 and 200 us, and preferably between 0.5 and 20 us.

The repetition frequency of the excitation signal should have a range between 0.5Hz and 20 kHz, and preferably between 1 Hz and 2 kHz.

The peak acoustic pressure amplitude should have a range between 50 KPa and 10 MPa, and preferably between 500 kPa and 5 MPa.

However, it is understood that other durations, repetition frequencies, and pressure amplitudes may be applied, provided that they excite and expand the selected microbubbles of the particular contrast agent used during the ultrasound examination.

The excitation ultrasound system 10 further comprises a conventional ultrasound system 30, shown in FIG. 6 in phantom. Typically, the conventional ultrasound system 30 includes a transmitter 22 that is driven by a pulser 14 for emitting an imaging ultrasound signal. This signal corresponds to known transmitted ultrasound signals for pulse-echo imaging used in conventional ultrasound systems.

In the present invention, the exciter element 28 and the pulser 12 are operatively coupled to the conventional ultrasound system 30. In operation, the exciter 28 transmits an exciter signal into an object to be imaged. The exciter signal excites and expands selected microbubbles contained in the object according to the invention as described in detail above.

The conventional ultrasound system 30 transmits its imaging ultrasound signal into the object to image the structures, and blood flow containing microbubbles within the object. The imaging signal is scattered (or echoed) by the structures, blood flow, and microbubbles, and is received by a receiver 24 where it is processed into an ultrasound image. Although the transmitter 22 and the receiver 24 are shown separately, it is understood that they can be combined into a single configuration.

A pulse controller 18 controls and coordinates the excitation, transmitting, and receiving steps of the present invention according to a timing schedule shown in FIGS. 11A, 11B, and 11C which are which is described in detail below.

The received imaging signal is then processed by the conventional ultrasound equipment 30. The imaging signal received by receiver 24 is amplified by amplifier 36 and converted into a digital signal by an analog-to-digital converter 38. The digital signal is provided to a preprocessing unit 32, and a postprocessing unit 34 for processing of the image which is displayed by a display unit 40.

Two processing methods are provided by the present invention for the production of an ultrasound image. In the first method, used when there is a difference in arrival time between the excitation signal and the imaging signal, the imaging signals received by the receiver 24 are gated through the pulse controller 18. The gating sequence used by the controller 18 is based upon the difference in arrival time between the excitation signal and the imaging signal.

The second method is used when the arrival time between the excitation signal and the imaging signal overlaps. In this method the received time-based imaging signal is processed through a Fourier transform and reduced into its frequency components. This process provides the invention with the ability to separate and filter out excitation signals from imaging signals including all harmonics. This process is accomplished in a preprocessor 32 incorporated into the conventional ultrasound equipment 30.

Transducers

Figure 7:
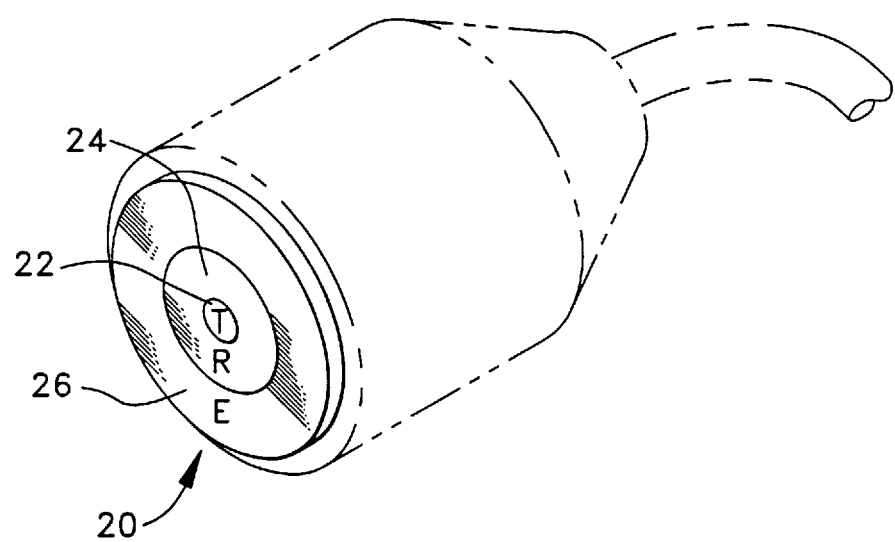
FIG. 7 is an illustration of a transducer according to the present invention.

FIG. 7 illustrates a transducer 20 according to a preferred embodiment of the present invention. In FIG. 7, an annular array aperture 20 has a first element 26 capable of emitting at least one excitation signal, and a second element 22 capable of emitting and receiving at least one imaging signal. Also shown in FIG. 7, is another aspect of the transducer 20 a wideband receiving element 24 capable of receiving harmonic components of the returning imaging signals.

Figure 8A:
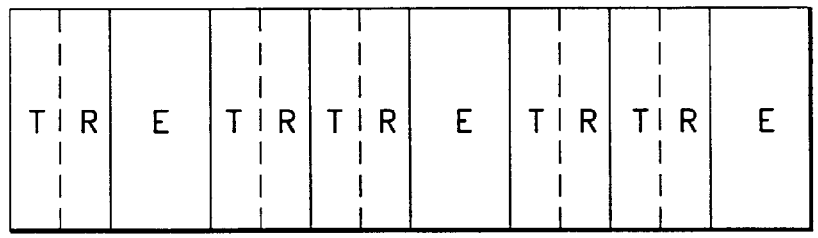
FIGS. 8A and 8B illustrate schematically a front and top view, respectively, of an alternative transducer according to the present invention.
Figure 8B:
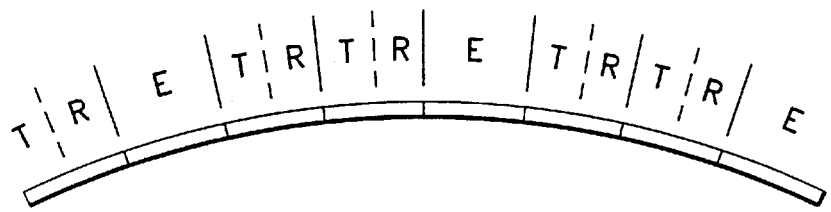
Figure 9A:
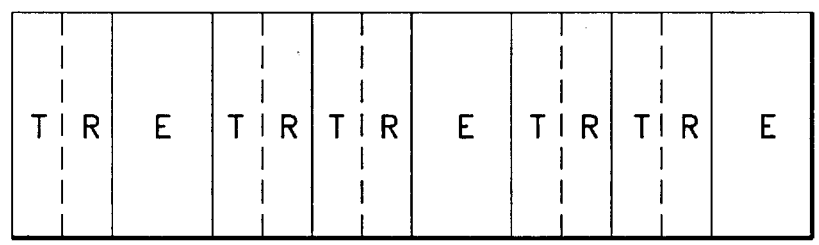
FIGS. 9A and 9B illustrate schematically a front and top view, respectively, of an alternative transducer according to the present invention.
Figure 9B:
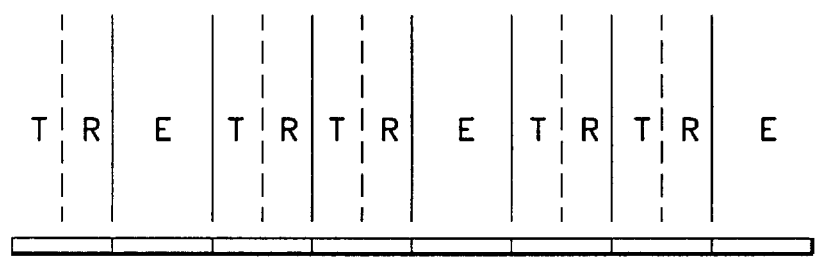

FIGS. 8A and 8B, 9A and 9B, and 10A and 10B illustrate schematically other embodiments of a transducer according to the invention. As shown in FIGS. 8A and 8B, a transducer has a series of conventional transducer, exciter, and wideband receiving elements configured in a non-planar configuration such as, but not limited to, a linear array. FIGS. 9A and 9B, show a transducer having a series of conventional transducer, exciter, and wideband receiving elements configured in a planar configuration such as, but not limited to, a linear array.

Figure 10A:
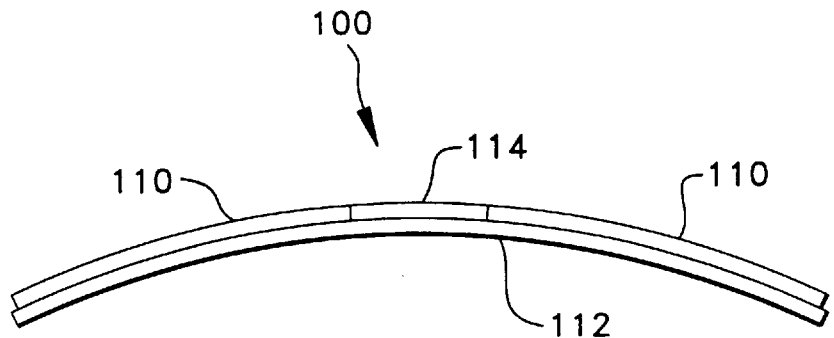
FIGS. 10A and 10B illustrate schematically a front and top view, respectively, of an alternative transducer according to the present invention.
Figure 10B:
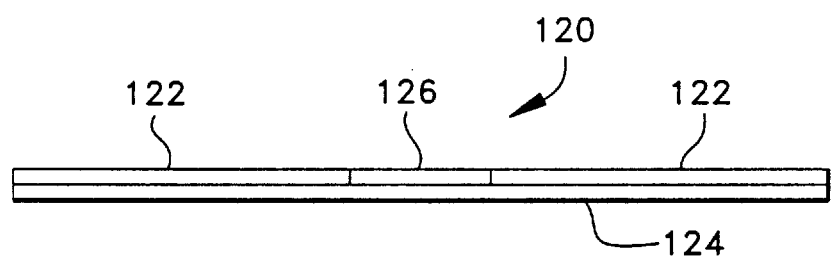

FIGS. 10A and 10B, show a transducer having at least two layers of conventional transducer, exciter, and wideband receiving elements configured in a non-planar array 100 and planar array 120, respectively.

In FIG. 10A a non-planar multi-layer array 100 is shown having an exciter element 114, image signal transmitting elements 110, and image signal receiving element 112. In FIG. 10B a planar multi-layer array 120 is shown having an exciter element 126, image signal transmitting elements 122, and image signal receiving element 124. It is understood that the receiving elements in all embodiments including receiving elements 112 and 122 be a wideband receiving elements.

It is understood that the elements of the transducer can be combined and adapted in any number of elements and shape as required, including an annular array, phased array, or linear array. In addition, each element can be single or multi-function, combining the functions of imaging transducer, exciter, and wideband receiver as required. For example, the wideband receiving capability of element 24 in FIG. 7 can be realized through a plurality of elements.

Pulse Sequencing

Figure 11A:
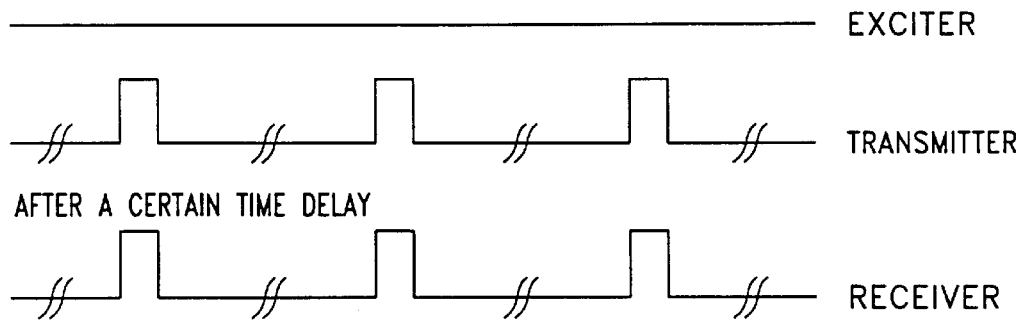
FIGS. 11A, 11B, and 11C illustrate acoustic pulse sequencing for exciter non-weighted imaging, weighted imaging, and blood pool imaging, respectively.
Figure 11B:
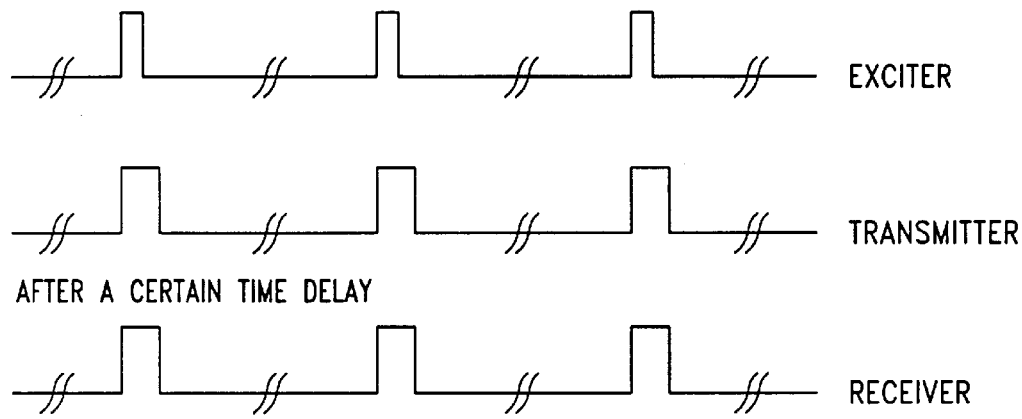
Figure 11C:
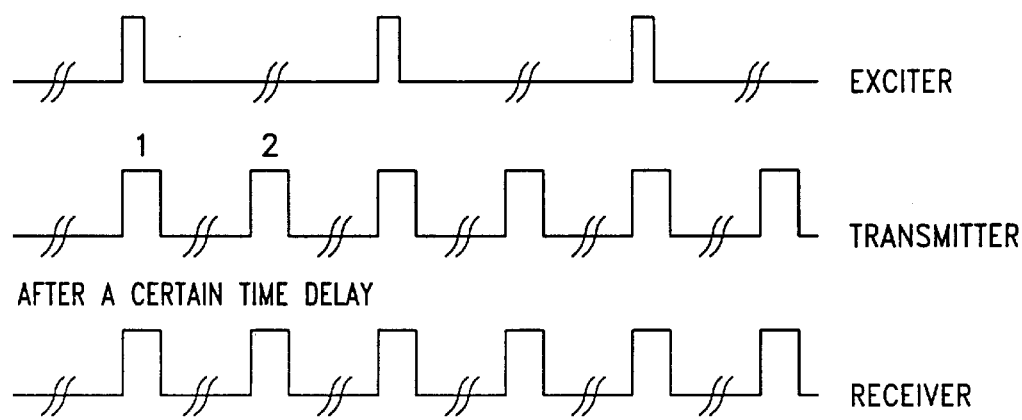

FIGS. 11A through 11C, illustrate examples of pulse sequences for achieving conventional (non-weighted), exciter-weighted, and blood pool imaging modes provided by the present invention.

Conventional Pulse-Echo (Non-weighted) Imaging

FIG. 11A illustrates the pulse sequencing for conventional (non-weighted) pulse-echo imaging. In FIG. 11A, the exciter is inactive and no sequencing is used. The transmitter and receiver sequencing is equivalent to the sequencing used in conventional ultrasound. In addition, the characteristics of the transmitter and receiver pulses, including center frequency, pulse width, repetition frequency, and amplitude, are equivalent to that used in conventional ultrasound equipment.

Weighted Pulse-echo Imaging

FIG. 11B illustrates the pulse sequencing for weighted pulse-echo imaging. In FIG. 11B, the exciter is excited by a short pulse having a pulse width between 0.5 and 20 us. Other characteristics of the pulse, such as pulse center frequency, amplitude, and pulse repetition frequency, are determined by the type of contrast agents used and the amount of enhancement required in the region of interest. It is desirable, however, to avoid having the center frequency of the exciter signal as a (sub-, ultra-, or super-harmonic) harmonic of the imaging signal.

Referring to FIG. 6, the pulse controller 18 commands the exciter 28 and the pulser 14 to emit at least one excitation signal to momentarily excite microbubbles within selected regions (tissue or blood) of interest during an ultrasound exam. Under excitation, the selected microbubbles oscillate and expand in size. As the microbubbles expand, their scattering capabilities increase an order of magnitude for a 30% uniform expansion of microbubble size as illustrated in FIG. 5.

Proximate with at least one excitation signal is at least one imaging signal is transmitted also within the selected regions (tissue or blood) of interest during an ultrasound exam. The excitation signals may lead or follow the excitation signals by 0 to 0.5. The imaging signals are scattered by the tissue or blood flow and the expanded microbubbles of the contrast agent within the tissue or blood flow. In those areas where the contrast agent is not present, the scattered signals returned by these regions will be of a significantly reduced intensity. Thus, in the exciter weighted imaging mode, only a region with a contrast agent is weighted (illuminated or intensified) while a region without the contrast agent remains the same as in conventional imaging.

Blood Pool Imaging

FIG. 11C illustrates pulse sequencing for blood pool imaging of blood flow, leakage, vessel blockage, or low blood flow. As shown in FIG. 11C, the exciter is pulsing on and off in order to provide an exciter weighted image as described above. When the exciter is off, the returned signal is non-weighted, providing a non-weighted image also described above. In selected regions of the body where no contrast agent is present, the signal returned by the exciter weighted mode, $S_{ew}$, is equivalent to that returned by the non-weighted mode, $S_{nw}$. In the regions of the body having contrast agents, the signal returned by the exciter weighted mode $S_{ew}$ is greater than that returned by the non-weighted mode $S_{nw}$.

By subtracting the signals produced by the two modes, $S_{ew}-S_{nw}$, an image of just the areas having the contrast agents can be produced. Equivalently, for contrast agents transported by blood flow, subtracting the two modes, $S_{ew}-S_{nw}$, an image of blood vessels and blood flow can be produced. Therefore, a significant feature of the present invention is its ability to image blood independent of its flow within the body. The subtraction process described in the imaging modes described above is carried out within the preprocessor 32 illustrated in FIG. 6.

Figure 12A:
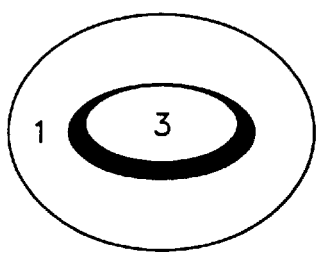
FIGS. 12A, 12B, and 12C illustrate, respectively, a conventional ultrasound non-weighted image, an exciter weighted image, and a blood pool image produced according to the present invention.
Figure 12B:
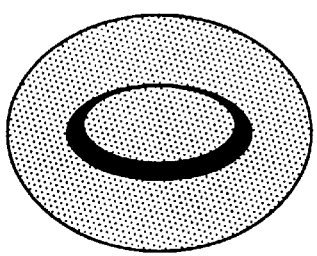
Figure 12C:
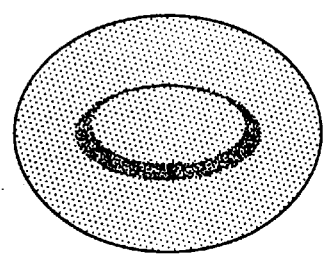

FIGS. 12A and 12B are representative of the images that can be produced by a display associated with the present invention. FIG. 12A shows an image produced from a signal $S_{nw}$ returned by the non-weighted mode. FIG. 12B shows an image produced from a signal $S_{ew}$ returned by the exciter weighted mode. FIG. 12C shows a difference image produced by subtracting the excited weighted signals from the conventional (non-weighted) signal, $S_{ew}-S_{nw}$.

The present invention addresses the problem of echogenecity in contrast microbubbles. Variations of echogenecity in contrast microbubbles are due to cyclic heart motion (Mor-Avi et al., *J. Am. Coll. Cardiol.,* 24(7), pp. 1779–1785, 1994). In another embodiment of the present invention, pulse sequences of the imaging signals are coordinated with an EKG detector by the pulse controller 18 to minimize the variation of echo strength produced by cyclic heart motion.

Harmonic Imaging

In another embodiment of the present invention, scattered and returned ultrasound signals are used to producing harmonic imaging of structures and blood flow in the body. Referring to FIG. 6, a transmitter 22 and a receiver 24 are used to receive the fundamental and harmonic components of the returned ultrasound signal. The receiver 24 is capable of receiving ultrasound signals having a frequency range between 0.5 and 15 MHz, and a pressure amplitude between 10 Pa and 7 MPa.

With this capability, the invention can receive and process an even greater amount of returned ultrasound energy and produce more detailed and accurate images. Signal components having a wide range of frequencies and pressures are processed by the preprocessing unit 32. The detected harmonic components of the imaging signal are used by the preprocessing unit and the postprocessing unit 34 to form a harmonic image with enhanced contrast discrimination of the surrounding structures in the body.

In all embodiments of the present invention, a conventional display 40, as shown in FIG. 6, is used to present an ultrasound systems image. In a preferred embodiment, a color coder (not shown) is added to the display 40 for displaying color data derived from the signal intensity or a Doppler shift detected by the invention. Imaging data and color display data are combined to enhance the contrast of the structures and blood flow detected by the "weighted" and "non-weighted" imaging modes.

Therapeutic Ultrasound

In another embodiment, the present invention can provide diagnostic and therapeutic capabilities. Referring to FIG. 6, the transmitter 22 and receiver 24 are used to form an ultrasound image for diagnosis. The exciter 28 is then used to provide the necessary acoustic field for ultrasound therapy. The exciter 28 emits an acoustic field having a preferred frequency range of 1 kHz to 5 MHz, a pressure range of 10 Pa to 10 MPa, a pulse repetition of 0.5 Hz to 20 kHz, and a duty cycle of 0.01 to 1.

Therapeutic ultrasound is particularly important in two situations. First, when applying therapeutic ultrasound it is often necessary to monitor the delivery of specific agents into specific target areas in the body. Second, once the agents have reached the target areas, it is then necessary to apply an acoustic field to activate the agents to induce/enhance the therapeutic effect. It can also be used in controlled long delivery situations.

The present invention may be embodied in other specific forms without departing from the spirit or essential attributes thereof and, accordingly, reference should be made to the appended claims, rather than to the foregoing specification, as indicating the scope of the invention.

What is claimed is:

1. An excitation enhanced ultrasound imaging system comprising:
    at least one exciter for transmitting an excitation signal capable of exciting microbubbles contained within an object, and
    an ultrasound imaging system in operative communication with said exciter, said ultrasound imaging system capable of transmitting at least one imaging signal separate from said excitation signal and being capable of receiving ultrasound imaging signals scattered and returned by microbubbles excited by said excitation system and said object, wherein said ultrasound imaging system produces an image from said received imaging signals using pulse-echo techniques.

2. The system of claim 1, wherein said exciter and said ultrasound imaging system are operatively coupled to a pulse controller, said pulse controller controlling the transmitting of said excitation signals and the receiving of said imaging signals according to a desired sequence.

3. The system of claim 1, wherein said exciter and said ultrasound system utilize a single aperture comprising at least one element capable of transmitting a said excitation signals, and further comprising at least one transducer element capable of transmitting and receiving said imaging signal.

4. The system of claim 3, wherein said at least one transducer element comprises a wideband elements capable of receiving harmonic components of said imaging signals.

5. The system of claim 1, wherein said excitation signal is a pulsed acoustic signal.

6. The system of claim 1, wherein said exciter comprises an excitation element and a pulser.

7. The system of claim 1, wherein said at least one exciter comprises a plurality of elements for transmitting a plurality excitation signals, and said ultrasound imaging system comprises at least one transmitting element and at least one wideband receiving element capable of receiving harmonic components of said imaging signals.

8. The system of claim 2, wherein said pulse controller controls the formation of exciter weighted imaging, blood pool imaging, and harmonic imaging.

9. The system of claim 2, wherein said pulse controller controls the transmission of said excitation signals and receiving of said imaging signals according to a desired sequence for diagnostic ultrasound.

10. The system of claim 2, wherein said pulse controller controls the transmission of said excitation signals and receiving of said imaging signals according to a desired sequence for therapeutic ultrasound.

11. An excitation enhanced ultrasound imaging system comprising:
    at least one exciter for transmitting an excitation signal capable of exciting microbubbles contained within an object,
    an ultrasound imaging system in operative communication with said exciter, said ultrasound imaging system capable of transmitting at least one imaging signal separate from said excitation signal and capable of receiving imaging signals that are scattered and returned by microbubbles excited by said excitation system and said object, and
    a pulse controller operatively coupled to said exciter and said ultrasound imaging system, said pulse controller controlling the transmission of said excitation signals and the receiving of said imaging signals according to a desired sequence, wherein said ultrasound imaging system produces an image from said received imaging signals using pulse-echo techniques.

12. A method for an excitation enhanced ultrasound imaging system comprising the steps of:
    exciting microbubbles with an exciter transmitting at least one excitation signal capable of exciting microbubbles contained in an object,
    imaging said microbubbles and said object with an ultrasound imaging system in operative communication with said exciter, said ultrasound imaging system capable of transmitting at least one imaging signal separate from said excitation signal and capable of receiving imaging signals that are scattered and returned by microbubbles excited by said excitation system and said object, and sequencing said excitation signals and said imaging signals with a pulse controller operatively coupled to said exciter and said ultrasound imaging system, said pulse controlling the transmission of said excitation signals and the receiving of said imaging signals according to a sequence, wherein said ultrasound imaging system produces an image from said received imaging signals using pulse-echo techniques.

* * * * *